US005705692A

United States Patent [19]
Wang et al.

[11] Patent Number: 5,705,692
[45] Date of Patent: Jan. 6, 1998

[54] PROCESS FOR THE PREPARATION OF IOHEXOL

[75] Inventors: Xiu C. Wang, Gurnee; Steve A. Chamberlin, Waukegan; Ashok V. Bhatia, Libertyville; Gregg E. Robinson, Skokie; John Hufnagel, Waukegan, all of Ill.

[73] Assignee: Abbott Laboratories, Abbott Park, Ill.

[21] Appl. No.: 721,431

[22] Filed: Sep. 27, 1996

[51] Int. Cl.⁶ ............. C07C 231/02; C07C 231/08; C07C 231/12; C07C 231/14
[52] U.S. Cl. ............................. 564/153; 564/139
[58] Field of Search ...................... 564/139, 153

[56] References Cited

U.S. PATENT DOCUMENTS 3,867,431  2/1975  Felder et al. ............... 260/501 A
4,001,323  1/1977  Felder et al. ............... 260/559 A
4,250,113  2/1981  Nordal et al. ............... 564/153
5,191,119  3/1993  Sovak et al. ............... 564/153

FOREIGN PATENT DOCUMENTS 532390  10/1984  Spain.
541191  12/1985  Spain.

OTHER PUBLICATIONS

J. Haavaldsen et al., "X-Ray Contrast Agents", *Chemistry Acta Pharm., Suec.* 20, 219–232 (1983).

*Primary Examiner*—Peter O'Sullivan
*Attorney, Agent, or Firm*—Gregory W. Steele

[57] ABSTRACT

Provided is a novel process for the preparation of iohexol having improved yields and purity, reduced number of isolated intermediates, and significantly reduced volume of ion-exchange resins required to desalinate the final product.

16 Claims, No Drawings

PROCESS FOR THE PREPARATION OF IOHEXOL

TECHNICAL FIELD OF THE INVENTION

This invention relates to a process for the preparation of iohexol.

BACKGROUND OF THE INVENTION

There exist a number of prior art methods for the production of iohexol (5-[Acetyl(2,3-dihydropropyl)amino]-N, N'-bis(2,3-dihydroxypropyl)-2,4,6-triiodo-1,3-benzenedicarboxamide; CAS-66108-95-0), see, for example, U.S. Pat. Nos. 4,250,113 and 5,191,119, Spanish patents ES 532 390 and ES 541 191, and Haavaldsen, et al, Acta Pharm. Suec. 20: 219–232 (1983). However, prior art procedures are not always amenable to large scale production as they may require inconvenient separation steps or the use of difficult to handle reagents and/or result in relatively low yields. For instance, Haavaldsen, et al utilize a multi-step procedure which isolates an intermediate by filtration from acetic anhydride/sulfuric acid. In addition, the yield from the first step is reported to be only 65%.

Another problem of existing methods is that in the final reaction step, the conversion of 5-acetamino-N,N'-bis-(2,3-dihydroxypropyl)-2,4,6-triiodobenzenedicarboxamide to iohexol, large quantities of sodium chloride can be produced. The removal of this salt thus requires ion-exchange resins resulting in increased cost and loss of product.

Thus there continues to be a need for an efficient method of producing iohexol with improved product purity.

BRIEF SUMMARY OF THE INVENTION

The present invention provides a process of producing iohexol wherein 5-amino-2,4,6-triiodoisophthalic acid dichloride, N,N-dimethylacetamide, or alternately, dimethylformamide (DMF), or 1-methyl-2-pyrrolidone and acetyl halide are combined to form a first reaction mixture, maintaining the first reaction mixture for a period of time sufficient to allow the reaction to proceed to completion, adding 3-amino-1,2-propanediol, N,N-dimethylacetamide (or DMF), and a base to the first reaction mixture to form a second reaction mixture, maintaining the second reaction mixture for a period of time sufficient for 5-acetamino-N,N'-bis-(2,3-dihydroxy-propyl)-2,4,6-triiodobenzene dicarboxamide formation, converting 5-acetamino-N,N'-bis-(2,3-dihydroxyl-propyl)-2,4,6-triiodobenzene dicarboxamide to iohexol in the presence of 3-chloro-, or 3-bromo-1,2-propanediol, lithium alkoxide or hydroxide and alcohol, and isolating iohexol by precipitation.

The present invention also provides a process of producing the intermediate 5-acetamino-N,N'-bis-(2,3-dihydroxy-propyl)-2,4,6-triiodobenzene dicarboxamide wherein 5-amino-2,4,6-triiodoisophthalic acid dichloride, acetyl halide, and a solvent selected from N,N-dimethylacetamide, dimethylformamide, or 1-methyl-2-pyrrolidone are combined to form a first reaction mixture, maintaining the first reaction mixture for a period of time sufficient to allow the reaction to proceed to completion, adding 3-amino-1,2-propanediol, N,N-dimethylacetamide (or DMF), and a base with the first reaction mixture to form a second reaction mixture, maintaining the second reaction mixture for a period of time sufficient for 5-acetamino-N,N'-bis-(2,3-dihydroxy-propyl)-2,4,6-triiodobenzene dicarboxamide formation, isolating the 5-acetamino-N,N'-bis-(2,3-dihydroxy-propyl)-2,4,6-triiodobenzene dicarboxamide so formed.

DETAILED DESCRIPTION OF THE INVENTION

The following terms and abbreviations are used throughout this specification and appended claims.

The term "butanol" means compounds of the formula $C_4H_{10}O$.

"DMA" means N,N-dimethylacetamide.

"DMF" means N,N-dimethylformamide.

"NMP" means 1-methyl-2-pyrrolidone.

"ATIPA-Cl" means 5-amino-2,4,6-triiodoisophthalic acid dichloride.

"APD" means 3-amino-1,2-propanediol.

"IPA" means isopropyl alcohol.

The term "3-CPD" means 3-chloro-1,2-propanediol.

All chemicals used are of reagent grade or better and are commercially available (e.g., Sigma Chemical Company, St. Louis, Mo., Aldrich Chemical Company, Milwaukee, Wis.)

The present invention relates to a process of producing iohexol from a commercially available raw material involving the isolation of only one intermediate compound. In accordance with the process of the invention, as described briefly here and in more detail below, Compound 1, 5-amino-2,4,6-triiodoisophthalic acid dichloride is converted to the corresponding N-acyl diamide, 5-acetamino-N,N'-bis-(2,3-dihydroxypropyl)-2,4,6-triiodobenzenedicarboxamide (compound 2), in high yield. Compound 2 is then converted to iohexol (Compound 3) in an additional reaction step. The present invention improves upon the prior art methods by (i) reducing the number of intermediates which must be isolated, (ii) providing improved yields of Compound 2, (iii) allowing for the isolation of both Compound 2 and Compound 3 without the need for removal of solvents (such as DMA, DMF, or propylene glycol) by vacuum distillation (processing steps which can result in decreased product purity), and (iv) formation of iohexol with the by-product lithium chloride (which can be substantially removed by recrystallization from lower alcohols) and thereby a significantly reduced volume of ion-exchange resins required to desalinate the final product.

In accordance with the first step of the process of the invention, 5-amino-2,4,6-triiodoisophthalic acid dichloride (Compound 1), solvent and acetyl halide, preferably acetyl chloride, are combined to form a reaction mixture that is maintained for a period of time sufficient for N-acylation to occur. Suitable solvents include DMA, DMF and NMP and may optionally include additional cosolvents such as acetonitrile, acetone, and the like. Typically, the reaction mixture is maintained at 20° to 40° C. for 4 to 18 hours, preferably 25° C. for 12 hours. Optionally, the extent of reaction can be monitored using techniques known in the art, such as in-process HPLC. The reaction mixture containing the resulting diacid dichloride product is quenched with lithium hydroxide (LiOH) and held on ice until any resulting exothermic reaction has subsided. At this point the resulting material can be optionally isolated by precipitation into water. Preferably, however, 3-amino-1,2-propanediol and base, preferably triethylamine, lithium alkoxide or lithium hydroxide, most preferably lithium hydroxide, are combined with the diacid chloride product as a single pot reaction and maintained for a period of time sufficient for N-acyl diamide formation. Typically, this step of the reaction is maintained at −10° to 50° C. for 6–18 hours, preferably 0° to 25° C. for 12 hours. Again, the extent of the reaction can be monitored as previously described. After completing of the reaction, the reaction mixture is added to an appropriate solvent, such as butanol, ethyl acetate/isopropyl alcohol (1–3:1), causing a precipitate of 5-acetamino-N,N'-bis-(2,3-dihydroxy-propyl)-2,4,6-triiodobenzene-dicarboxamide (Compound 2) to form. This crude solid is resuspended in water, the pH adjusted to approximately 5, then concentrated by atmospheric distillation. After cooling, the resulting cake is washed with alcohol, collected and dried under vacuum.

This step of the process of the invention can be, and preferably is, advantageously carried out as a one-pot reaction, thus resulting in Compound 2 of consistently high purity and recovery, typically greater than 98% and 65 to 80%, respectively.

In accordance with the second step of the process of the invention, Compound 2, is conveniently converted to iohexol (Compound 3) by the addition of 3-chloro-1,2-propanediol, optionally 3-bromo-1,2-propanediol, in the presence of a base and alcohol. Suitable bases include sodium, potassium and lithium alkoxides and hydroxides. The alkoxides of thes bases can optionally be prepared from the metal and a suitable alcohol. Preferably, the base is again lithium alkoxide or lithium hydroxide, most preferably lithium hydroxide and the alcohol is a lower alkyl alcohol, preferably methanol or ethanol. The reaction is allowed to proceed until completion and results in a very high conversion of starting material to iohexol, typically on the order of greater than 95%. The use of methanol as the solvent is conveniently conducted at room temperature with the resulting iohexol precipitating from solution as it is added to isopropyl alcohol. It has also been discovered that the use of ethanol as the solvent allows for direct precipitation of iohexol while the reaction proceeds under reflux conditions.

The second step of the process of the invention avoids the use of sodium methoxide, and resulting sodium chloride, as taught in the prior art.

The resulting iohexol can be collected and further purified using techniques well known in the art. For instance, by recrystallization from butanol as described in U.S. Pat. No. 4,250,113, which is incorporated by reference.

The following Examples illustrate embodiments of the invention and are not intended to limit the specification and claims in any way.

EXAMPLE 1a

Preparation of 5-acetamino-N,N'-bis-(2,3-dihydroxy-propyl)-2,4,6-triiodobenzene dicarboxamide (Compound 1)

240 gm. of 5-amino-2,4,6-triiodoisophthalic acid dichloride (ATIPA-Cl) was dissolved in 290 gm. DMA. The reaction flask was placed in an ambient temperature bath and charged with 45 gm. acetyl chloride in rapid drops. After 24 hours the mixture was cooled to less than 5° C. 19.3 gm. of lithium hydroxide (anhydrous) and 60 gm. DMA were charged to the reaction mixture. The mixture was maintained in an ice bath until the resulting exotherm had subsided and the internal temperature was less than 5° C.

3-Amino-1,2-propanediol (3-APD, 100 gm), DMA (70 gm), and anhydrous lithium hydroxide (19.3 gm) were combined in a 1 L flask and cooled to less than 5° C. The diacid chloride/DMA mixture was added to the 3-APD/DMA mixture maintaining the internal temperature of the latter at less than 20° C. The initial reaction flask was rinsed with DMA (16 gm), with the rinse charged to the 3-APD/DMA mixture. The mixture was warmed gradually to ambient temperature. After the reaction was judged complete, the reaction mixture was diluted with isopropanol (IPA, 300 gm) and mixed until homogeneous.

Ethyl acetate (900 gm) and IPA (900 gm) were combined and heated to 50° C. The reaction mixture was charged in rapid drops over 20 minutes. The resulting slurry was cooled to less than 5° C. and mixed for 1 hour. The pH of the mixture was adjusted to 5–6 with acetic acid (19 gm). The solids were collected by centrifugation, with each load being washed with IPA (80 gm).

The collected wetcake was suspended in distilled water (1.5 L). After adjusting the pH of the mixture to 5–6 with concentrated hydrochloric acid (HCl) the mixture was distilled atmospherically until the internal temperature exceeded 98° C. The slurry was cooled gradually to less than 5° C., then mixed for 2 hours. The solids were collected by centrifugation, with each load being washed with methanol (120 gm). The collected solids were dried to a constant weight of 215 gm under vacuum at 100° C. HPLC analysis showed purity of >98% of the desired compound.

As an alternate to suspension of the crude wetcake in water, the collected wetcake (120 gm. ATIPA-Cl charge) is heated to reflux with water (300 gm.) and ethanol (700 gm.). If necessary, the pH can be adjusted to 5 to 6 with concentrated HCl. The mixture is refluxed for 16 hours and then gradually cooled to less than 5° C. while maintaining the temperature with continuous mixing for one hour. The mixture is filtered and the cake washed with ethanol. The collected solids are then dried under vacuum at 100° C. to a constant weight. HPLC analysis showed purity of >97.5% of the desired compound.

EXAMPLE 1b

Alternate procedure for the preparation of 5-acetamino-N,N'-bis-(2,3-dihydroxy-propyl)-2,4,6-triiodobenzene dicarboxamide (Compound 1)

300 gm. ATIPA-Cl is dissolved in 415 gm. DMA. The reaction flask is placed in an ambient temperature bath and charged with 67.5 gm. acetyl chloride. After the reaction is judged complete, 7 mL of water is charged to the mixture. The reaction solution is mixed for 15 minutes then charged to a second flask containing 119 gm. of 3-APD, 260 gm. DMA, and 200 gm. triethylamine while maintaining the temperature of the contents at less than 10° C. The mixture is warmed slowly to 25° C. After the reaction is judged complete, the precipitated triethylammonium HCl is removed by filtration. The filtered solution is charged to 3.6 L of 65° C. ethyl acetate/isopropanol. The resulting slurry is cooled to <5° C. and the solids are collected, then slurried in 1.5 L of water. The mixture is concentrated by atmospheric distillation until the internal temperature exceeds 98° C. After cooling to <5° C., the solids are collected, washed with 300 mL methanol and dried to 280 gm. of Compound 2.

EXAMPLE 2a

Converting 5-acetamino-N,N'-bis-(2,3-dihydroxypropyl)-2,4,6-triiodobenzenedicarboxamide to iohexol 5-Acetamino-N,N'-bis-(2,3-dihydroxypropyl)-2,4,6-triiodobenzenedicarboxamide (Example 1, 50 gm), anhydrous lithium hydroxide (2.89 gm) and methanol (75 gm) were combined and heated under nitrogen until dissolution of solids was complete. The mixture was cooled to less than 5° C. 3-Chloro-1,2-propanediol (10.6 mL) was added in rapid drops. The mixture was allowed to warm to ambient temperature over several hours. After 36 hours of mixing, HPLC analysis showed 97.5% iohexol (sum of "endo" and "exo") and less than 0.5% remaining starting material. The solution was neutralized with concentrated HCl and then added to IPA. The solids formed were filtered and dried under vacuum to give 92% of iohexol.

EXAMPLE 2b

Alternate procedure for the conversion of 5-acetamino-N,N'-bis-(2,3-dihydroxypropyl)-2,4,6-triiodobenzenedicarboxamide to iohexol 5-Acetamino-N,N'-bis-(2,3-dihydroxypropyl)-2,4,6-triiodobenzenedicarboxamide (Example 1, 20 gm), lithium ethoxide (11.6 gm.), and ethanol (180 mL) are mixed and heated to 70° C. The mixture is cooled to 20° C. and 3-chloropropanediol (24.6 mL) is added. The mixture is refluxed for five hours. The pH is adjusted to 6 with concentrated hydrochloric acid. Most of the solvent is evaporated and isopropanol (200 mL) is added. The mixture is stirred at 0° to 5° C., filtered and the cake washed with isopropanol. The solid is dried under vacuum at 50° C. The dried crude iohexol weighed 13.6 gm. (61.9% yield).

We claim:

1. A process for making iohexol comprising the steps of:
   a. combining 5-amino-2,4,6-triiodoisophthalic acid dichloride, acetyl halide, and a solvent selected from N,N-dimethylacetamide, dimethylformamide, or 1-methyl-2-pyrrolidone to form a first reaction mixture;
   b. maintaining the first reaction mixture for a period of time sufficient to allow the reaction to proceed to completion;
   c. combining 3-amino-1,2-propanediol, N,N-dimethylacetamide, and a base with the first reaction mixture to form a second reaction mixture;
   d. maintaining the second reaction mixture for a period of time sufficient for 5-acetamino-N,N'-bis-(2,3-dihydroxy-propyl)-2,4,6-triiodobenzene dicarboxamide formation;
   e. converting 5-acetamino-N,N'-bis-(2,3-dihydroxypropyl)-2,4,6-triiodobenzene dicarboxamide to iohexol in the presence of 3-chloro-1,2-propanediol or 3-bromo-1,2-propanediol, base and alcohol; and
   f. isolating the iohexol.

2. The process of claim 1 wherein step (a) uses N,N-dimethylacetamide.

3. The process of claim 1 wherein the acetyl halide is acetyl chloride or acetyl bromide.

4. The process of claim 3 wherein the acetyl halide is acetyl chloride.

5. The process of claim 1 wherein the base of step (c) is lithium hydroxide, lithium alkoxide, lithium carbonate, triethylamine, sodium carbonate, potassium carbonate, and 3-amino-1,2-propanediol.

6. The process of claim 1 wherein the lithium base of step (e) is lithium hydroxide or lithium alkoxide.

7. The process of claim 1 wherein the alcohol of step (e) is methanol or ethanol.

8. The process of claim 7 wherein the alcohol is methanol and the iohexol is precipitated in the presence of isopropyl alcohol, butanol, ethyl acetate, acetonitrile, acetone, or an alcohol of 3–8 carbon atoms.

9. The process of claim 7 wherein the alcohol is ethanol.

10. The process of claim 1 further comprising the step of collecting the 5-acetamino-N,N'-bis-(2,3-dihydroxypropyl)-2,4,6-triiodobenzene dicarboxamide.

11. The process of claim 10 wherein the collecting includes precipitating the 5-acetamino-N,N'-bis-(2,3-dihydroxy-propyl)-2,4,6-triiodobenzene dicarboxamide in ethyl acetate, butanol, acetonitrile, isopropanol, or mixtures thereof.

12. The process of claim 11 further comprising recrystallization of 5-acetamino-N,N'-bis-(2,3-dihydroxy-propyl)-2,4,6-triiodobenzene dicarboxamide.

13. The process of claim 12 wherein the recrystallization of 5-acetamino-N,N'-bis-(2,3-dihydroxy-propyl)-2,4,6-triiodobenzene dicarboxamide comprises solubilizing the precipitate in water followed by the addition of alcohol sufficient to cause the 5-acetamino-N,N'-bis-(2,3-dihydroxy-propyl)-2,4,6-triiodobenzene dicarboxamide to precipitate.

14. The process of claim 8 wherein the iohexol is precipitated in the presence of isopropyl alcohol.

15. A process for making iohexol comprising the steps of:
   a. combining 5-amino-2,4,6-triiodoisophthalic acid dichloride, acetyl chloride and N,N-dimethylacetamide to form a first reaction mixture;
   b. maintaining the first reaction mixture for four to eighteen hours to allow the reaction to proceed to completion;
   c. combining 3-amino-1,2-propanediol, N,N-dimethylacetamide, and lithium hydroxide with the first reaction mixture to form a second reaction mixture;
   d. maintaining the second reaction mixture for six to eighteen hours to form 5-acetamino-N,N'-bis-(2,3-dihydroxy-propyl)-2,4,6-triiodobenzene dicarboxamide;
   e. adding the reaction mixture to ethyl acetate and isopropanol to precipitate the 5-acetamino-N,N'-bis-(2,3-dihydroxy-propyl)-2,4,6-triiodobenzene dicarboxamide;
   f. converting the 5-acetamino-N,N'-bis-(2,3-dihydroxy-propyl)-2,4,6-triiodobenzene dicarboxamide to iohexol in the presence of lithium hydroxide and methanol; and
   g. isolating the iohexol.

16. A process for making 5-acetamino-N,N'-bis-(2,3-dihydroxy-propyl)-2,4,6-triiodobenzene dicarboxamide comprising the steps of:
   a. combining 5-amino-2,4,6-triiodoisophthalic acid dichloride, acetyl halide, and a solvent selected from N,N-dimethylacetamide, dimethylformamide, or 1-methyl-2-pyrrolidone to form a first reaction mixture;
   b. maintaining the first reaction mixture for a period of time sufficient to allow the reaction to proceed to completion;
   c. combining 3-amino-1,2-propanediol, N,N-dimethylacetamide, and a base with the first reaction mixture to form a second reaction mixture;
   d. maintaining the second reaction mixture for a period of time sufficient for 5-acetamino-N,N'-bis-(2,3-dihydroxy-propyl)-2,4,6-triiodobenzene dicarboxamide formation;
   e. isolating the 5-acetamino-N,N'-bis-(2,3-dihydroxy-propyl)-2,4,6-triiodobenzene dicarboxamide so formed.

* * * * *